United States Patent [19]

Field et al.

[11] Patent Number: 5,001,140

[45] Date of Patent: Mar. 19, 1991

[54] CYCLOALKYLTHIAZOLES

[75] Inventors: George F. Field, Danville, Calif.; John R. Vermeulen, Wanaque; William J. Zally, Cresskill, both of N.J.

[73] Assignee: Hoffmann-La Roche Inc., Nutley, N.J.

[21] Appl. No.: 366,097

[22] Filed: Jun. 13, 1989

Related U.S. Application Data

[63] Continuation-in-part of Ser. No. 339,046, Apr. 17, 1989, abandoned, which is a continuation-in-part of Ser. No. 226,112, Jul. 15, 1988, abandoned.

[51] Int. Cl.$^5$ .................. C07D 277/30; A61K 31/425
[52] U.S. Cl. ................................ 514/365; 548/204
[58] Field of Search ...................... 548/204; 514/365

[56] References Cited

U.S. PATENT DOCUMENTS

| | | | |
|---|---|---|---|
| 4,749,701 | 6/1988 | Hayashi et al. | 514/247 |
| 4,866,071 | 9/1989 | Pettit | 514/287 |

FOREIGN PATENT DOCUMENTS

| | | | |
|---|---|---|---|
| 0219436 | 4/1987 | European Pat. Off. | 514/247 |
| 0228959 | 7/1987 | European Pat. Off. | 514/247 |

*Primary Examiner*—Robert Gerstl
*Attorney, Agent, or Firm*—George M. Gould; Bernard S. Leon; William G. Isgro

[57] ABSTRACT

The invention relates to compounds of the formula:

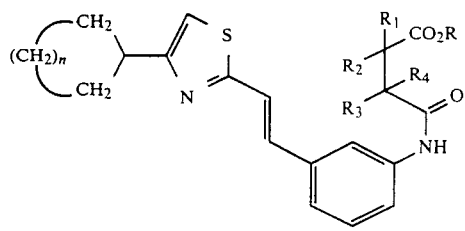

wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy or halogen, or $R_1$ and $R_2$ taken together with the carbon atom are alkylene of 2 to 5 carbon atoms unsubstituted or substituted by lower alkyl, and n is an integer of from 0 to 3, and, when $R_1$ is different from $R_2$ and/or when $R_3$ is different from $R_4$, enantiomers, diastereomers and racemates thereof and, when R is hydrogen, salts thereof with pharmaceutically acceptable bases.

The compounds of formula I and, when R is hydrogen, pharmaceutically exceptable salts thereof are useful as bronchopulmonary agents, for example, in the relief of asthma and allergic reactions.

18 Claims, No Drawings

CYCLOALKYLTHIAZOLES

CROSS-REFERENCE TO RELATED APPLICATION

This application is a continuation-in-part of U.S. Ser. No. 07/339,046, filed Apr. 17, 1989, which in turn is a continuation-in-part of U.S. application Ser. No. 226,112, filed July 15, 1988.

BRIEF SUMMARY OF THE INVENTION

The invention relates to compounds of the formula

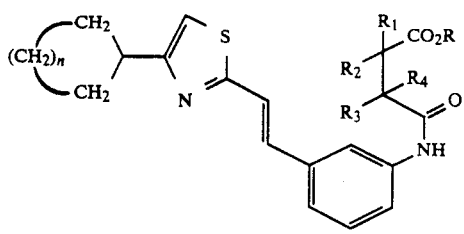

wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy, or halogen, or $R_1$ and $R_2$ taken together with the carbon atom are alkylene of 2 to 5 carbon atoms unsubstituted or substituted by lower alkyl, and n is an integer of from 0 to 3, and, when $R_1$ is different from $R_2$, and/or when $R_3$ is different from $R_4$, enantiomers, diastereomers and racemates thereof, and, when R is hydrogen, salts thereof with pharmaceutically acceptable bases.

The compounds of formula I and pharmaceutically acceptable salts thereof are useful as bronchopulmonary agents, for example, in the relief of asthma and allergic reactions.

In another aspect, the invention relates to pharmaceutical compositions, methods of using the compound of formula I and intermediates.

DETAILED DESCRIPTIONOF THE INVENTION

The invention relates to compounds of the formula

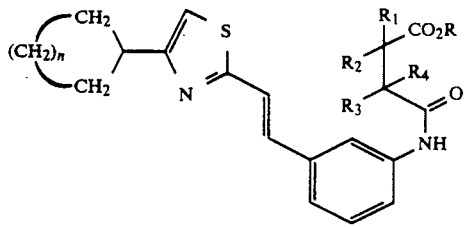

wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy, or halogen, or $R_1$ and $R_2$ taken together with the carbon atom are alkylene of 2 to 5 carbon atoms unsubstituted or substituted by lower alkyl, and n is an integer of from 0 to 3, and, when $R_1$ is different from $R_2$, and/or $R_3$ is different from $R_4$, enantiomers diastereomers and/or racemates thereof and, when R is hydrogen, salts thereof with pharmaceutically acceptable bases.

As used herein, the term "lower alkyl" preferably denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "lower alkenyl" denotes a straight or branched chain saturated hydrocarbon containing 3 to 7 carbon atoms, for example, propenyl, butenyl, pentenyl, hexenyl and the like. Exemplary of "alkylene of 2 to 5 carbon atoms" are ethylene, propylene, butylene and pentylene. The term "cycloalkyl" denotes a cyclic alkyl group of 3 to 6 carbon atoms, for example cyclopropyl, cyclopentyl, cyclohexyl and the like. The term "halogen" denotes chlorine, bromine, iodine and fluorine.

The compounds of formula I and their salts exist as the (E) or trans geometric isomers. As used herein, the term "the compounds of formula I" shall include enantiomers, diastereomers and racemic mixtures thereof, when $R_1$ is different from $R_2$, and/or $R_3$ is different from $R_4$.

A preferred group of the compounds of formula I are those wherein R is hydrogen, $R_1$ and $R_2$, independently, are lower alkyl $R_3$ and $R_4$ are hydrogen and n is 0 to 3.

A more preferred group of compounds of formula I are those wherein R is hydrogen $R_1$ and $R_2$,independently, are lower alkyl, $R_3$ and $R_4$ are hydrogen, and n is 1.

Preferred compounds of formula I of the invention are:
(E)-4-[[3-[2-(4-cyclobutyl-2-thiazolyl)ethenyl]phenyl]amino]-2,2-diethyl-4-oxobutanoic acid; and
(E)-4-[[3-[2-(4-cyclopropyl-2-thiazolyl)ethenyl]phenyl]amino]-2,2-diethyl-4-oxobutanoic acid.

Exemplary of the compounds of formula I of the invention are:
(E)-4-[[3-[2-(4-cyclopropyl-2-thiazolyl)ethenyl]phenyl]amino]-2,2-dipropyl-4-oxobutanoic acid;
(E)-4-[[3-[2-(4-cyclopropyl-2-thiazolyl)ethenyl]phenyl]amino]-2,2-dihexyl-4-oxobutanoic acid;
(E)-4-[[3-[2-(4-cyclopropyl-2-thiazolyl)ethenyl]phenyl]amino]-2-methyl-2-propyl-4-oxobutanoic acid;
(E)-4-[[3-[2-(4-cyclopropyl-2-thiazolyl)ethenyl]phenyl]amino]-2-ethyl-2-propyl-4-oxobutanoic acid;
(E)-4-[[3-[2-(4-cyclopropyl-2-thiazolyl)ethenyl]phenyl]amino]-2-butyl-4-oxobutanoic acid;
(E)-4-[[3-[2-(4-cyclopropyl-2-thiazolyl)ethenyl]phenyl]amino]-2-(2-butyl)-4-oxobutanoic acid;
(E)-2-butyl-4-[[3-[2-(4-cyclobutyl-2-thiazolyl)ethenyl]phenyl]amino]-2-ethyl-4-oxobutanoic acid;
(E)-4-[[3-[2-(4-cyclobutyl-2-thiazolyl)ethenyl]phenyl]amino]-2-ethyl-2-methyl-4-oxobutanoic acid;
(E)-4-[[3-[2-(4-cyclobutyl-2-thiazolyl)ethenyl]phenyl]amino]-2-(1,1-dimethylethyl)-4-oxobutanoic acid;
(E)-4-[[3-[2-(4-cyclohexyl-2-thiazolyl)ethenyl]phenyl]amino]-2-hexyl-2-methyl-4-oxobutanoic acid;
(E)-4-[[3-[2-(4-cyclobutyl-2-thiazolyl)ethenyl]phenyl]amino]-2-(2-propenyl)-4-oxobutanoic acid;
(E)-4-[[3-[2-(4-cyclobutyl-2-thiazolyl)ethenyl]phenyl]amino]-2-cyclopentyl-4-oxobutanoic acid;
(E)-4-[[3-[2-(4-cyclopropyl-2-thiazolyl)ethenyl]phenyl]amino]-3,3-dipropyl-4-oxobutanoic acid;
(E)-4-[[3-[2-(4-cyclopropyl-2-thiazolyl)ethenyl]phenyl]amino]-3,3-diethyl-4-oxobutanoic acid;
(E)-4-[[3-[2-(4-cyclopropyl-2-thiazolyl)ethenyl]phenyl]amino]-2,2-dipropyl-4-oxobutanoic acid;

(E)-4-[[3-[2-(4-cyclopropyl-2-thiazolyl)ethenyl]phenyl]amino]-2,2-dihexyl-4-oxobutanoic acid;
(E)-4-[[3-[2-(4-cyclopropyl-2-thiazolyl)ethenyl]phenyl]amino]-2-methyl-2-propyl-4-oxobutanoic acid;
(E)-4-[[3-[2-(4-cyclopropyl-2-thiazolyl)ethenyl]phenyl]amino]-2-ethyl-2-propyl-4-oxobutanoic acid;
(E)-4-[[3-[2-(4-cyclopropyl-2-thiazolyl)ethenyl]phenyl]amino]-2-butyl-4-oxobutanoic acid;
(E)-4-[[3-[2-(4-cyclopropyl-2-thiazolyl)ethenyl]phenyl]amino]-2-(2-butyl)-4-oxobutanoic acid;
(E)-4-[[3-[2-(4-cyclobutyl-2-thiazolyl)ethenyl]phenyl]amino]-2-ethyl-4-oxobutanoic acid;
(E)-4-[[3-[2-(4-cyclobutyl-2-thiazolyl)ethenyl]phenyl]amino]-2-ethyl-2-methyl-4-oxobutanoic acid;
(E)-4-[[3-[2-(4-cyclobutyl-2-thiazolyl)ethenyl]phenyl]amino]-2-(1,1-dimethylethyl)-4-oxobutanoic acid;
(E)-4-[[3-[2-(4-cyclohexyl-2-thiazolyl)ethenyl]phenyl]amino]-2-hexyl-2-methyl-4-oxobutanoic acid ethyl ester;
(E)-4-[[3-[2-(4-cyclobutyl-2-thiazolyl)ethenyl]phenyl]amino]-2-(2-propenyl)-4-oxobutanoic acid;
(E)-4-[[3-[2-(4-cyclobutyl-2-thiazolyl)ethenyl]phenyl]amino]-2-cyclopentyl-4-oxobutanoic acid;
(E)-4-[[3-[2-(4-cyclopropyl-2-thiazolyl)ethenyl]phenyl]amino]-3,3-dipropyl-4-oxobutanoic acid;
(E)-4-[[3-[2-(4-Cyclopropyl-2-thiazolyl)ethenyl]phenyl]amino]-3,3-diethyl-4-oxobutanoic acid methyl ester; and the like.

The compounds of formula I can be prepared as hereinafter described in Reaction Schemes I, II, III and IV.

corresponding compound of formula III in the presence of an alkanol, for example, methanol, and a halogenating agent, for example, bromine, at a temperature in the range of from about 10° C. to about room temperature. The resulting compound of formula III can be recovered utilizing known procedures, for example, distillation, chromatography and the like. Alternatively, the compound of formula III can be utilized in situ in the next reaction step.

The compound of formula IV, which is a known compound, is converted to the compound of formula V by treatment with a thiolating agent, for example, phosphorus pentasulfide or Lawesson's reagent in the presence of an inert solvent, for example, a hydrocarbon, such as, toluene or the like, at the reflux temperature of the reaction mixture. The resulting compound of formula V can be recovered utilizing known procedures, for example, crystallizarion, chromatography and the like.

Thereafter, a compound of formula III is reacted with the compound of formula V conveniently in the presence of an inert solvent, for example, an alkanol, such as, ethanol, or the like, at a temperature in the range of from about 0° C. to about 100° C. A resulting compound of formula VI can be recovered utilizing known procedures, for example, crystallization, chromatography and the like.

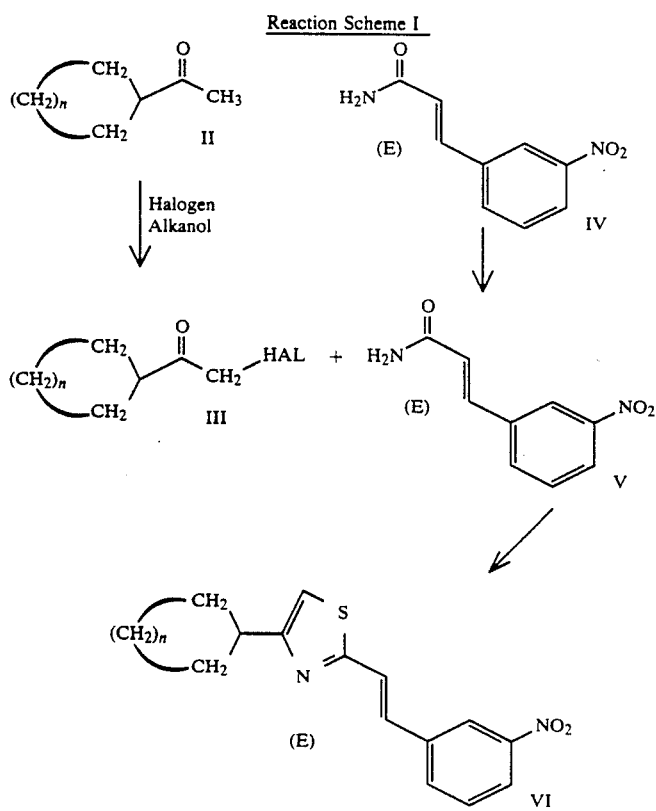

wherein n is as previously described and HAL is halogen.

In Reaction Scheme I, a compound of formula II, which are known compounds or can be prepared according to known procedures, is halogenated to the

Reaction Scheme II

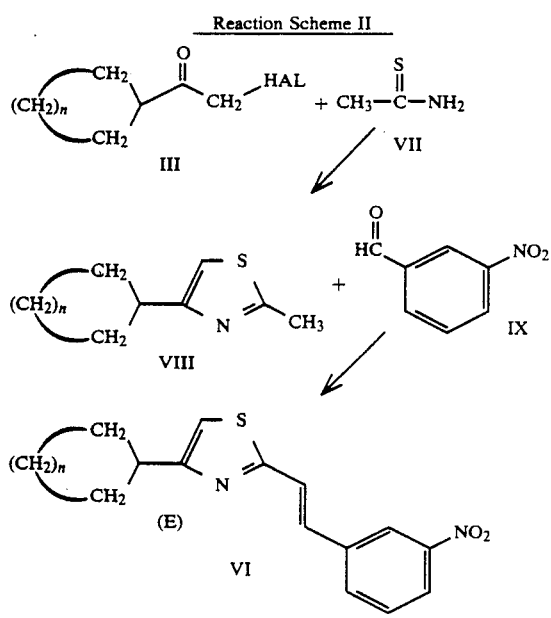

when n is as previously described and HAL is halogen.

In Reaction Scheme II, a compound of formula III, is reacted with the compound of formula VII, which is a known compound, to give the corresponding compound of formula VIII. The reaction is conveniently carried out in the presence for an inert solvent, for example, an alkanol, such as, ethanol, at a temperature in the range of from about 0° C. to about 100° C. The resulting compound of formula VIII can be recovered utilizing known procedures, for example, distillation, chromatography and the like.

A compound of formula VIII is reacted with the compound of formula IX, which is a known compound, in the presence of a dehydrating agent, for example, acetic anhydride and the like, at a temperature in the range of from about 0° C. to about 150° C., to yield the corresponding compound of formula VI. The resulting compound of formula VI can be recovered utilizing known procedures, for example, distillation, chromatography and the like.

Reaction Scheme III

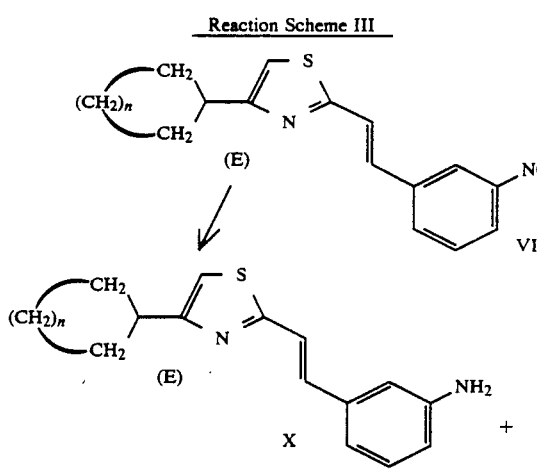

-continued
Reaction Scheme III

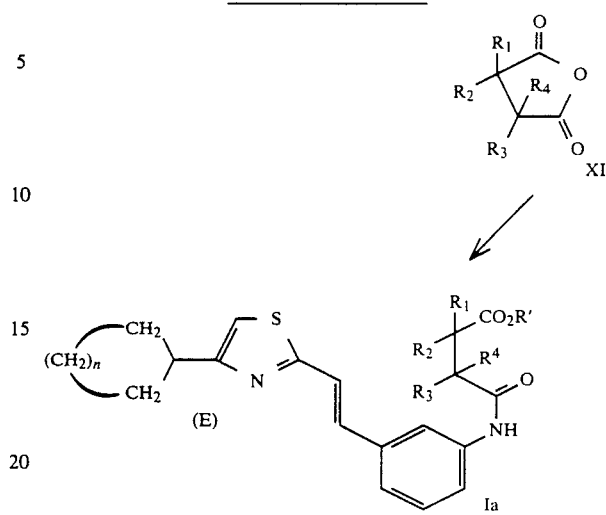

wherein R' is hydrogen, and $R_1$, $R_2$, $R_3$, $R_4$ and n are as previously described.

In Reaction Scheme III, a compound of formula VI is reduced to the corresponding compound of formula X by utilizing a reducing agent, for example, stannous chloride, Raney Nickel with hydrogen and the like in the presence of an inert solvent, for example, an alkanol, such as, ethanol, at a temperature is in the range of from about 0° C. to about 100° C. The resulting compound of formula X can be recovered utilizing known procedures, for example, extraction, chromatography and the like.

A compound of formula X is reacted with a compound of formula XI, which are known compounds or can be prepared by known procedures, in an inert solvent, for example, a halogenated hydrocarbon, such as, methylene chloride, an ether, such as, 1,2-dimethoxyethane and the like, optionally in the presence of a base, for example, sodium acetate, at a temperature in the range of from about −10° C. to about 100° C. to yield the corresponding compound of formula Ia. The resulting compound of formula Ia can be recovered by known procedures, for example, crystallization, chromatography and the like.

Reaction Scheme IV

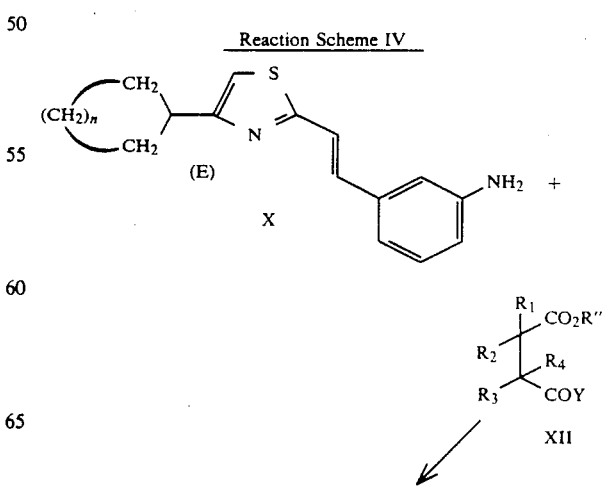

-continued
Reaction Scheme IV

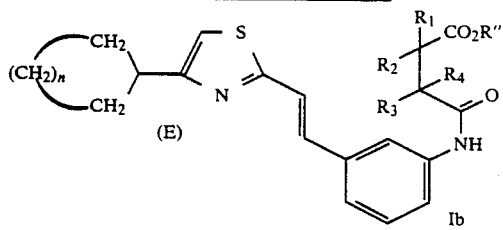

wherein R" is lower alkyl, Y is a leaving group, such as, halogen, hydroxyl or the like, and $R_1$, $R_2$, $R_3$, $R_4$ and n are as previously described.

In Reaction Scheme IV, a compound of formula X is acylated with a compound of formula XII, wherein Y is halogen, which are known compounds or can be prepared by known procedures, in an inert solvent, for example, a halogenated hydrocarbon, such as, methylene chloride and the like, at a temperature in the range of from about $-10°$ C. to about 50° C.

Alternatively, a compound of formula X is acylated with a compound of formula XII, wherein Y is hydroxyl, which are known compounds or can be prepared by known procedures, in an inert solvent, for example, a halogenated hydrocarbon, such as, methylene chloride and the like, at a temperature in the range of from about $-10°$ C. to about 50° C., and in the presence of an activating agent, for example, dicyclohexylcarbodiimide and the like. The resulting compound of formula Ib can be recovered by known procedures, for example, crystallization, chromatography and the like.

Reaction Scheme V

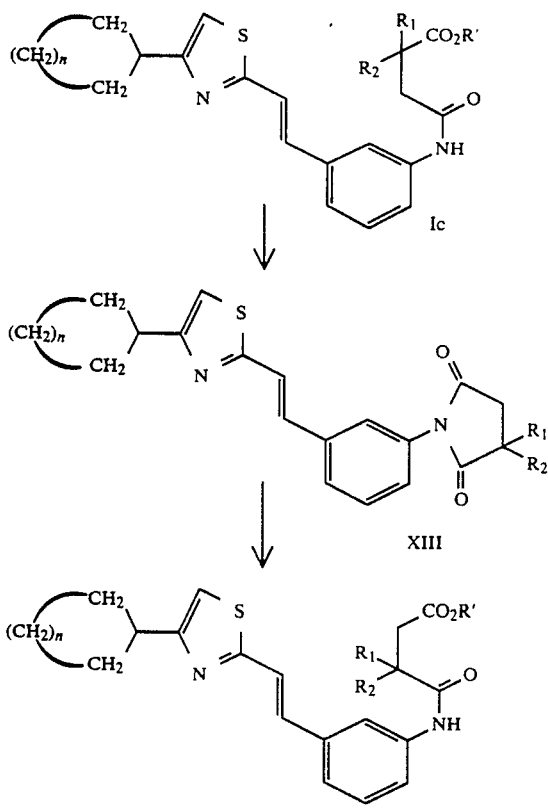

wherein R', $R_1$, $R_2$ and n are as previously described, except that at least one of $R_1$ and $R_2$ must be other than hydrogen.

In Reaction Scheme V, a compound of formula Ic can be transaminated to the corresponding compound of formula Id by first cyclizing a compound of formula Ic with a dehydrating agent, for example, an acid chloride such as acetyl chloride or the like, with or without a solvent, such as toluene or methylene chloride, at reflux.

The resulting product of formula XIII can be used without purification or it can be isolated by standard procedures, such as crystallization or the like and then cleaved with a base, such as with an alkali metal or alkaline earth metal hydroxide such as lithium hydroxide or the like, in the presence of an aqueous/organic solvent such as water/methanol or the like and at a temperature in the range of from about 25° to about 100° C.

Thereafter, the resulting compound of formula Id, after acidification with an acid such as hydrochloric acid or the like, can be isolated by standard procedures, such as crystallization or the like.

The invention also relates to the salts of the compounds of formula I, their enantiomers, diastereomers and racemates thereof wherein R is hydrogen, which salts can be prepared by the reaction of the said compounds with a base having a non-toxic, pharmaceutically acceptable cation. In general, any base which will form a salt with a carboxylic acid and whose pharmacological properties will not cause an adverse physiological effect when ingested is considered as being within the scope of this invention. Suitable bases thus include, for example, the alkali metal and alkaline earth metal hydroxides and carbonates, ammonia, primary, secondary and tertiary amines, such as, monoalkylamines, dialkylamines, trialkylamines, nitrogen containing heterocyclic amines, for example, piperidine and the like.

The compounds of formula I and, when R is hydrogen, their pharmaceutically acceptable salts are active as inhibitors of bronchoconstriction and are therefor useful as bronchopulmonary agents, for example, in the relief of asthma and allergic reactions. The useful activity of the compounds of formula I of the invention can be demonstrated as hereinafter set forth.

LEUKOTRIENE $D_4$ RECEPTOR BINDING ASSAY (GUINEA PIG LUNG HOMOGENATE)

(1) Methods (a) Preparation of membrane Homogenate

Male albino guinea pigs (Hartley strain, 400–500 g body weight) were sacrificed by decapitation. The lungs were removed, frozen in liquid nitrogen and stored at $-70°$ until use. The frozen tissue (5 g) was thawed, minced into small pieces and rinsed in phosphate-buffered saline. The tissue was placed in 40 ml homogenization buffer containing 0.25 M sucrose, 10 mM Tris-HCl, (pH 7.5), and the following protease inhibitors: soybean trypsin inhibitor (5 μg/ml) bacitracin (100 μg/ml), benzamidine ($10^{-3}$M) and phenylmethylsulfonyl fluoride ($10^4$M). The protease inhibitors were included to inhibit proteolysis during the processes of homogenization and centrifugation. The tissue was then homogenized at 0°–4° C. with a Brinkman PT-20 polytron for a total of 1 minute (10 second pulses at a setting of 6). The homogenate was centrifuged ($1000 \times g$ for 10 minutes) to remove tissue clumps, unbroken cells and nuclei. The supernatant was recentrifuged at 30,000×g for 30 minutes to yield pellets which were referred to as crude membrane fractions. This fraction was then resuspended in the incubation buffer (10 mM pipes buffer, pH 7.5, 50 mM NaCl), homogenized in a Teflon homogenizer and recentrifuged at 30,000×g for 30minutes. The pellets were finally resuspended in the incubation buffer with a Teflon homogenizer at a concentration of 10 to 20 mg/ml of protein in the suspension. The concentrations of proteins were determined using the Biorad reaction kit.

(b) Receptor-Ligand Binding Assay

Optimum assay conditions were determined with an assay mixture containing: Tyrode solution; 0.1% bovine serum albumin (BSA); 1 mM glycine; 1 mM cysteine; 3.5 nM $^3$H-LTD$_4$ and the membrane preparation (100-200 μg protein) in a final volume of 250 μl. The incubation was carried out at 20° C. for 30 minutes. At 20° C., binding increased linearly with protein concentration, reached equilibrium in 20 minutes, was saturable, and reversible upon additions of unlabelled LTD$_4$.

(1.2 mg/kg) administered intravenously, and the animals were ventilated with a Harvard (Model #680) small animal respirator set a 40 breaths/min and 4.0 cc stroke volume. Control vehicle or test drug was administered through the cannula into the jugular vein 1 minute before the animals were challenged intravenously with a maximum constrictory dose of LTD (25 μg/kg) given intravenously. The change in tracheal pressure was averaged for control and drug-treated animals and percent inhibition was calculated. For determination of oral activity, animals were dosed with test compound or vehicle two hours prior to challenge with LTD (25 μg/kg, i.v.).

The relative potency (ID$_{50}$ values) of test compounds administered by the intravenous and oral route was determined by administering increasing doses of test compound. For determination of the time course of inhibition for various compounds, the time between administration of compound and challenge with LTD was varied. The time course of activity was calculated as the time when inhibition decreased to 40%.

TABLE I

| Compound | LTD$_4$ Binding IC$_{50}$(μM) | % Inhibition at 1 mg/kg i.v. (ID$_{50}$) | LTD$_4$-Induced Bronchoconstriction % Inhibition at 10 mg/kg p.o. (ID$_{50}$) | Duration 10 mg/kg p.o. | | |
|---|---|---|---|---|---|---|
| | | | | 4 hr. | 8 hr. | 18 hr. |
| (E)-4-[[3-[2-(4-cyclopropyl-2-thiazolyl)ethenyl]phenyl]amino]-2,2-diethyl-4-oxobutanoic acid | 0.020 | 94 ± 2 (0.18) | 98 ± 1 (1.1) | 99 ± 1 | 95 ± 1 | 61 ± 6 |
| (E)-4-[[3-[2-(4-cyclopropyl-2-thiazolyl)ethenyl]phenyl]amino]-4-oxobutanoic acid | 4.0 | 15 ± 4 | — | — | — | — |
| (E)-4-[[3-[2-(4-cyclopentyl-2-thiazolyl)ethenyl]phenyl]amino]-2-methylene-4-oxobutanoic acid | 0.200 | — | 27 ± 3 | — | — | — |
| (E)-4-[[3-[2-(4-cyclopentyl-2-thiazolyl)ethenyl]phenyl]amino]-2,2-diethyl-4-oxobutanoic acid | 0.060 | 99 ± 1 (0.08) | 97 ± 1 (0.34) | 99 ± 1 | 98 ± 1 | 70 ± 7 |
| (E)-4-[[3-[2-(4-cyclohexyl-2-thiazolyl)ethenyl]phenyl]amino]-2,2-diethyl-4-oxobutanoic acid | 0.080 | 96 ± 2 (0.31) | 87 ± 6 (0.66) | 69 ± 12 | 81 ± 9 | 38 ± 4 |
| (E)-4-[[3-[2-(4-cyclobutyl-2-thiazolyl)ethenyl]phenyl]amino]-2,2-diethyl-4-oxobutanoic acid | 0.015 | 98 ± 0 (0.13) | 99 ± 1 (0.12) | 100 ± 0 | 98 ± 1 | — |
| (E)-4-[[3-(2-(4-cyclobutyl-2-thiazolyl)ethenyl]phenyl]amino]-2-methyl-4-oxobutanoic acid | 0.110 | (0.61) | — | — | — | — |

Separation of bound from free $^3$H-LTD$_4$ was performed by rapid filtration on GF/C glass fiber filters and washing with two 4 ml aliquots of Tyrode solutions containing 0.1% BSA. Radioactivity remaining on the filters was measured in 10 ml of Aquasol. Specific binding was defined as that displaced by $10^{-6}$M unlabelled LTD$_4$ and was 95% of total binding.

LEUKOTRIENE-INDUCED BRONCHOCONSTRICTION IN GUINEA PIGS—IN VIVO LEUKOTRIENE D$_4$ (LTD) ANTAGONIST TEST

Intravenous and Oral Testing

Male guinea pigs (Hartley strain Charles River) weighing 300-500 g were anesthetized with urethane (~2 g/kg) intraperitoneally and a polyethylene cannula was inserted into the jugular vein for intravenous drug administration. Tracheal pressure (cm of H$_2$O) was recorded from a Statham pressure transducer (P 32 AA). Propranolol was administered 5 minutes prior to challenge with LTD. Two minutes later spontaneous breathing was arrested with succinylcholine chloride A compound of formula I, an enantiomer, a diastereomer or racemate thereof or a salt thereof or a composition containing a therapeutically effective amount of a compound of formula I, an enantiomer, a diastereomer or racemate thereof or a salt thereof can be administered by methods well known in the art. Thus, a compound of formula I, an enantiomer, a diastereomer or racemate thereof or a salt thereof can be administered either singly or with other pharmaceutical agents, for example, antihistamines, mediator release inhibitors, methyl xanthines, beta agonists or antiasthmatic steroids such as prednisone and prednisoline, orally, parenterally, rectally, or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized compositons. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 5 to about 1000 mg per day, preferably about 5 to about 250 mg either as a single dose or in divided doses.

The compounds of formula I of the invention, when $R_1$ and $R_2$ and/or $R_3$ and $R_4$ are different, possess one or two asymmetric carbon atom, they can thus be obtained as enantiomers, diastereomeric or as racemic mixtures. The diastereomeric mixtures can be separated by conventional methods. The resolution of racemates into the optically active isomers can be carried out by known procedures. Some racemic mixtures can be precipitated as eutectics and can thereafter be separated. Chemical resolution is, however, preferred. By this method, diastereomeric salts are formed from the racemic mixture of a compound of formula I, with an optically active resolving agent, for example, an optically active base, such as D-(+)-α-methylbenzylamine, which can be reacted with a carboxyl group. The formed diastereomers are separated by selective crystallization and converted to the corresponding optical isomer. Thus, the invention covers the racemates of the compounds of formula I as well as their optically active isomers (enantiomers).

The examples which follow further illustrate the invention. All temperatures are in degrees celsius unless otherwise stated.

EXAMPLE 1

Preparation of
(E)-4-[[3-[2-(4-cyclopropyl-2-thiazolyl)ethenyl]phenyl]amino]-2,2-diethyl-4-oxobutanoic acid To a solution of 25 g (92 mmol) of the compound of Example 9 in 100 ml of ethanol was added a solution of 75 g (0.33 mol) of stannous chloride dihydrate in 100 ml of ethanol. This mixture was stirred and heated under reflux for 1.5 hr. It was cooled to room temperature, made strongly alkaline (pH 13) by the addition of 3 N sodium hydroxide, and extracted with methylene chloride in three portions. The organic extracts were dried over magnesium sulfate and concentrated in vacuo. The residue was chromatographed on alumina using ethyl acetate as eluant to yield 12.6 g (53%) of the (E)-3-[2-[4-cyclopropyl)-2-thiazolyl]ethenyl]benzene amine as an oil.

A mixture of 3.5 g (20 mmol) of 2,2-diethylsuccinic acid and 10 ml of acetyl chloride was heated under reflux for 2 hr, cooled, and concentrated in vacuo. The residue was reconcentrated three times with toluene and then dissolved in 50 ml of 1,2-dimethoxyethane. This solution was added to a mixture of 2.5 g (10 mmol) of the crude amine in 50 ml of 1,2-dimethoxyethane and 4.1 g (50 mmol) of anhydrous sodium acetate. This mixture was heated on the steam bath for 2 hr and then filtered hot. The filtrate was concentrated in vacuo. The residue was digested with 500 ml of water on the steam bath for 0.25 hr. The solid was collected and recrystallized from 50 ml of aq. ethanol to give 2.5 g of (E)-4-[[3-[2-(4-cyclopropyl-2-thiazolyl)-ethenyl]phenyl]amino]-2,2-diethyl-4-oxobutanoic acid as off-white needles. Two more recrystallizations from aqueous ethanol gave 0.25 g, mp 153°–157° d.

Anal. Calcd for $C_{22}H_{26}N_2O_3S$: C, 66.31; H, 6.58; N, 7.03. Found: C, 66.47; H, 6.60; N, 7.00.

EXAMPLE 2

Preparation of
(E)-4-[[3-[2-(4-cyclopropyl-2-thiazolyl)-ethenyl]-phenyl]amino]-4-oxobutanoic acid A mixture of 2.5 g (10 mmol) of (E)-3-[2-[4-(cyclopropyl)-2-thiazolyl]ethenyl]benzeneamine prepared as in example 1 as above, 1.5 g (15 mol) of succinic anhydride, 1.64 g (20 mmol) of anhydrous sodium acetate and 200 ml of 1,2-dimethoxyethane was stirred and heated under reflux for 2 hr. The reaction mixture was cooled and concentrated in vacuo. The residue was heated on the steam bath with 200 ml of water for 0.5 hr. The solid was collected and recrystallized from ethanol to give 1.4 g of (E)-4-[[3-[2-(4-cyclopropyl-2-thiazolyl)-ethenyl]phenyl]amino]-4-oxobutanoic acid, mp 177°–179° dec, as off-white needles.

Anal. Calcd for $C_{18}H_{18}N_2O_3S$: C, 63.14; H, 5.30; N, 8.18. Found: C, 63.10; H, 5.01; N, 8.23.

EXAMPLE 3

Preparation of
(E)-4-[[3-[2-(4-cyclopentyl-2-thiazolyl)-ethenyl]phenyl]amino]-2,2-diethyl-4-oxobutanoic acid A mixture of 5.23 g (30 mmol) of 2,2-diethylsuccinic acid and 15 ml of acetyl chloride was heated under reflux for 3 hr, cooled, and concentrated in vacuo. The residue was reconcentrated twice with toluene and then dissolved in 75 ml of 1,2-dimethoxyethane. This solution was added to a mixture of 4.06 g (15 mmol) of (E)-3-[2-[4-cyclopentyl)-2-thiazolyl]ethenyl]benzene amine in 75 ml of 1,2-dimethoxyethane and 6.0 g (73 mmol) of anhydrous sodium acetate. This mixture was heated on the steam bath for 2 hr and then filtered hot. The filtrate was concentrated in vacuo. The residue was digested with 100 ml of water on the steam bath for ¼ hr. The solid was collected and rinsed with water to give 9.6 g of damp solid. This solid was recrystallized from 700 ml of acetonitrile to give 3.42 g (53%) of (E)-4-[[3-[2-(4-cyclopentyl-2-thiazolyl)ethenyl]phenyl]amino]-2,2-diethyl-4-oxobutanoic acid, mp 172°–174°.

Anal. Calcd for $C_{21}H_{30}N_2O_3S$: C, 67.58; H, 7.09; N, 6.57. Found: C, 67.27; H, 7.20; N, 6.70.

EXAMPLE 4

Preparation of
(E)-4-[[3-[2-(4-cyclohexyl-2-thiazolyl)-ethenyl]phenyl]amino]-2,2-diethyl-4-oxobutanoic acid A mixture of 9.26 g (53 mmol) of 2,2-diethylsuccinic acid and 30 ml of acetyl chloride was heated under reflux for 1.5 hr, cooled, and concentrated in vacuo. The residue was reconcentrated twice with toluene and then dissolved in 150 ml of 1,2-dimethoxyethane. To this solution was added 7.56 g (26.4 mmol) of the (E)-3-[2-[4-(cyclohexyl)-2-thiazolyl]-ethenyl]benzeneamine and 10.9 g of sodium acetate dissolved in 150 ml of 1,2-dimethoxyethane. This reaction mixture was heated on the steam bath for 3.5 hr and then concentrated in vacuo. The residue was digested with 600 ml of water on the steam bath for 20 min. The solid was collected to give 10 g of crude product. Recrystallization from ethanol gave 3.5 g of product, mp 180°–185°. Further recrystallization from methanol gave (E)-4-[[3-[2-(4-cyclohexyl-2-thiazolyl)-ethenyl]phenyl]amino]-2-methylene-4-oxobutanoic acid as off-white needles, mp 187°–189°.

Anal. Calcd for $C_{25}H_{32}N_2O_3S$: C, 68.15; H, 7.32; N, 6.36. Found: C, 67.87; H, 7.15; N, 6.36.

EXAMPLE 5

Preparation of
(E)-4-[[3-[2-(4-Cyclobutyl-2-thiazolyl)-ethenyl]phenyl]amino]-2,2-diethyl-4-oxobutanoic acid A mixture of 8.4 g (48 mmol) of 2,2-diethylsuccinic acid and 30 ml of acetyl chloride was heated under reflux for 2 hr, cooled, and concentrated in vacuo. The residue was reconcentrated twice with toluene and then dissolved in 125 ml of 1,2-dimethoxyethane. The solution was added to a mixture of 6.1 g (24 mmol) of (E)-3-[2-[4-(cyclobutyl)-2-thiazolyl]ethenyl]benzeneamine, 9.72 g (118 mmol) of sodium acetate and 125 ml of 1,2-dimethoxyethane, and the mixture was stirred and heated under reflux for 2 hr. It was filtered hot. The filtrate was concentrated in vacuo to leave 15.47 g of oil. This oil was triturated with 350 ml of hot water, and the solid collected. Recrystallization from methanol gave 1.4 g of (E)-4-[[3-[2-(4-cyclobutyl-2-thiazolyl)-ethenyl]phenyl]amino]-2,2-diethyl-4-oxobutanoic acid as off-white prisms, mp 170°–172°.

Anal. Calcd for $C_{23}H_{28}N_2O_3S$: C, 66.96; H, 6.84; N, 6.79. Found: C, 66.72; H, 6.79; N, 6.67.

EXAMPLE 6

Preparation of
(E)-4-[[3-[2-(4-cyclobutyl-2-thiazolyl)-ethenyl]phenyl]amino]-2-methyl-4-oxobutanoic acid A mixture of 6.34 g (48 mmol) of methylsuccinic acid and 30 ml of acetyl chloride was heated under reflux for 2 hr, cooled, and concentrated in vacuo. The residue was reconcentrated twice with toluene and then dissolved in 125 ml of 1,2-dimethoxyethane. The solution was added to a mixture of 6.1 g (24 mmol) of (E)-3-[2-[4-(cyclobutyl)-2-thiazolyl]ethenyl]benzeneamine, 9.72 g (118 mmol) of sodium acetate and 125 ml of 1,2-dimethoxyethane, and the mixture was stirred and heated under reflux for 2 hr. It was filtered hot. The filtrate was concentrated in vacuo to leave 14.2 g of oil. This oil was triturated with 400 ml of hot water for 20 minutes and then allowed to stand over the weekend. The solid was collected. Recrystallization from acetonitrile gave (E)-4-[[3-[2-(4-cyclobutyl-2-thiazolyl)-ethenyl]phenyl]amino]-2-methyl-4-oxobutanoic acid as off-white prisms, mp 165°–167°.

Anal. Calcd for $C_{20}H_{22}N_2O_3S$: C, 64.84; H, 5.99; N, 7.56. Found: C, 64.79; H, 5.92; N, 7.61.

EXAMPLE 7

Preparation of 4-Cyclopropyl-2-methylthiazole

A mixture of 80 g (0.49 mol) of bromomethylcyclopropylketone, 40.5 g (0.54 mol) of thioacetamide and 600 ml of ethanol was stirred and heated under reflux for 4 hr. and then allowed to stand overnight at room temperature. It was concentrated to dryness in vacuo and then reconcentrated after the addition of toluene. The residue was slurried with ether. The ether was decanted. Ether was added to the residue and then carefully treated with saturated sodium bicarbonate solution. The aqueous phase was separated and reextracted with ether. The organic phases were combined, washed with brine, dried over magnesium sulfate and concentrated in vacuo to leave 60 g of an amber oil. A solution of this oil in methylene chloride was filtered through a plug of Florisil using more methylene chloride to wash the plug. The eluates were concentrated in vacuo to give 44.1 g (65%) of 4-cyclopropyl-2-methylthiazole as a yellow oil.

EXAMPLE 8

Preparation of
(E)-4-cyclopropyl-2-[2-(3-nitrophenyl)-ethenyl]thiazole (a) From 4-Cyclopropyl-2-methylthiazole and m-nitrobenzaldehyde A mixture of 41.7 g (0.3 mole) of 4-cyclopropyl-2methylthiazole, 45.3 g (0.3 mol) of m-nitrobenzaldehyde and 15 ml of acetic anhydride was stirred and heated at 145°–165° under nitrogen for 17 hr. This reaction mixture was cooled and concentrated in vacuo. The residue was partitioned between water and methylene chloride. The organic layer was separated. dried over sodium sulfate and concentrated in vacuo to leave a black oil. This oil was dissolved in ethyl acetate, and the solution applied to 1 kg of Florisil which was eluted with ethyl acetate. The eluates were concentrated in vacuo to give 30 g (37 %) of crude product, mp 90°–95°. Recrystallization from ethyl acetate gave yellow needles, mp 92°–94°.

Anal. Calcd for $C_{14}H_{12}N_2O_2S$: C, 61.75; H, 4.44; N, 10.29. Found: C, 61.71; H, 4.49: N, 10.19.

(b) From m-nitrothiocinnamide and bromoacetylcyclopropane

A mixture of 16 g (0.098 mol) of bromoacetylcyclopropane, 100 ml of ethanol and 11.2 (0.054 mol) of m-nitrothiocinnamide was heated to reflux for 20 min. at which time TLC (25% ethyl acetate/hexane on silica plates) showed no thioamide left. The reaction mixture was stirred for 0.5 hr and then concentrated in vacuo. The residual solid was collected with ether. The solid was partitioned between water, ammonia and ether. The aqueous phase was extracted with 100 ml of ether. The combined organic extracts were washed with water and with brine, dried over sodium sulfate and concentrated in vacuo. The residual was crystallized from hexane to give 10.55 g (71%) of (E)-4-cyclopropyl-2-[2-(3-nitrophenyl)-ethenyl]thiazole as crude product.

EXAMPLE 9

Preparation of
(E)-4-Cyclobutyl-2-[2-(3-nitrophenyl)-ethenyl]thiazole

A mixture of 11 g (62 mmol) of bromoacetylcyclobutane, 12.9 g (62 mmol) of m-nitrothiocinnamide and 110 ml of ethanol was stirred and heated under reflux for 0.5 hr. The reaction mixture was collected and concentrated in vacuo. The residue was slurried with ether and the solid collected. This solid was shaken with water and ether. The aqueous phase was made alkaline by the addition of concentrated ammonium hydroxide. The organic phase was separated and the aqueous phase extracted with ether. The combined organic phases were washed with water and with brine, dried over sodium sulfate and concentrated in vacuo to give 14.67 g (82%) of crude product. Recrystallization of a small sample from acetonitrile gave (E)-4-cyclobutyl-2-[2-(3-nitrophenyl)ethenyl]thiazole as pale yellow needles, mp 78°–80°.

Anal. Calcd for $C_{15}H_{14}N_2O_2S$: C, 62.92; H, 4.93; N, 9.78. Found: C, 62.74; H, 4.88; N, 9.71.

EXAMPLE 10

Preparation of
(E)-4-cyclopentyl-2-[2-(3-nitrophenyl)-ethenyl]thiazole

A mixture of 11 g (57 mmol) of crude bromoacetylcyclopentane, 10 g (48 mmol) of m-nitrothiocinnamide and 75 ml of ethanol was heated on the steam bath for about 5 min at which time the thiocinnamide was largely in solution. After a solid had precipitated the reaction mixture was allowed to stand at room temperature for 2 days. The solid was collected and rinsed with ethanol to give 14 g of crude damp hydrobromide. This salt was distributed between 100 ml of methylene chloride and 50 ml of saturated sodium bicarbonate solution to which a few ml of concentrated ammonium hydroxide were added. The organic layer was separated, dried over sodium sulfate and concentrated in vacuo. The residue was crystallized from hexane to give 10.6 g (73%) of crude product, mp 65°–70°. Recrystallization from acetonitrile gave (E)-4-cyclopentyl-2-[2-(3-nitrophenyl)-ethenyl]thiazole as yellow spars, mp 68°–70°.

Anal. Calcd for $C_{16}H_{16}N_2O_2S$: C, 63.98; H, 5.37; N, 9.33. Found: C, 63.94; H, 5.25; N, 9.28.

EXAMPLE 11

Preparation of
(E)-4-cyclohexyl-2-[2-(3-nitrophenyl)-ethenyl]thiazole

A mixture of 5.02 g (24.5 mmol) of m-nitrothiocinnamide, 5.6 g (27 mmol) of crude bromomethylcyclohexylketone, and 40 ml of ethanol was stirred and heated under reflux for 5.3 hr. TLC (25% ethyl acetate/hexane on silica gel) showed thioamide still present. A further 5 ml of crude bromoketone was added to the reaction mixture for 0.5 hr when TLC showed no thioamide left. The reaction mixture was cooled, concentrated in vacuo and reconcentrated after addition of toluene to the residue. The resultant yellow solid was slurried with ether and collected. It was then partitioned between ether and water made alkaline by the addition of concentrated ammonium hydroxide. The organic layer was separated, dried over sodium sulfate and concentrated in vacuo. The residue was collected with hexane to give 5.6 g (73%) of product as a yellow solid. Recrystallization from hexane gave (E)-4-cyclohexyl-2-[2-(3-nitrophenyl)-ethenyl]thiazole as yellow needles, mp 102°–104°.

Anal. Calcd for $C_{17}H_{18}N_2O_2S$: C, 64.94; H, 5.77; N, 8.91. Found: C, 65.01; H, 5.68; N, 8.81.

EXAMPLE 12

Preparation of m-Nitrocinnamide

A mixture of 19.3 g (0.1 mol) of m-nitrocinnamic acid, 80 ml of thionyl chloride and 0.5 ml of dimethyl formamide was heated under reflux for 5 hr and then allowed to stand overnight at room temperature. The reaction mixture was concentrated to dryness in vacuo and reconcentrated after the addition of toluene. The solid residue was slurried with ether and collected to give 20.4 g of crude acid chloride. This solid was slowly added with stirring to 200 ml of concentrated ammonium hydroxide. After the mixture had stirred for 0.5 hr the solid was collected and air dried to give 18.13 g (94%) of m-nitrocinnamide, mp 189–191.

EXAMPLE 13

Preparation of m-Nitrothiocinnamide (a) A mixture of 40.38 g (0.21 mol) of m-nitrocinnamide, 42.5 g (0.105 mol) of Lawesson's reagent (2,4-bis(4-methoxyphenyl)-1,3-dithia-2,4-diphosphetane-2,4-disulfide), and 500 ml of 1,2-dimethoxyethane was stirred and heated under reflux for 2 hr, cooled to room temperature and concentrated to dryness in vacuo. The residue was slurried with 300 ml of methylene chloride and collected to give 24.61 g (56%) of product, mp 196°–197°. Recrystallization from acetonitrile gave an analytical sample as orange needles, mp 200°–202°.

Anal. Calcd. for $C_9H_8N_2O_2S$: C, 51.91; H, 3.87; N, 13.45. Found: C, 51.85; H, 3.82; N, 13.52.

(b) A mixture of 3.4 g (17.7 mmol) of m-nitrocinnamide, 1.96 g (8.8 mmol) of phosphorus pentasulfide, 1.5 g (17.7 mmol) of sodium bicarbonate and 100 ml of acetonitrile (5 drops of pyridine) was stirred and heated under reflux for 3 hr and poured on to ice water. After 1 hr of stirring the solid was collected to give 2.75 (75%) of m-nitrothiocinnamide as crude product, mp 187°–189°.

EXAMPLE 14

Preparation of 2,2-diethylsuccinic anhydride

A mixture of 3.5 g (20 mol) of 2,2-diethylsuccinic acid and 10 ml of acetyl chloride was heated under reflux for 2 hr, cooled, concentrated in vacuo, and reconcentrated three times after the addition of toluene. The residue was used without further purification.

EXAMPLE 15

Preparation of 2,2-diethylsuccinic acid

To a stirred mixture of 186 g (1 mol) of ethyl 2-cyano-3,3-diethylacrylate and 800 ml of 50 % aqueous ethanol was added 98 g (2 mol) of sodium cyanide. The sodium cyanide slowly dissolved (exotherm). After stirring at room temperature for 0.5 hr the solution was heated on the steam bath for 5 min., cooled, diluted with 2 l of water and made acid by the addition of concentrated hydrochloric acid. This mixture was extracted with $3 \times 1$ l of methylene chloride. The organic extracts were combined, dried over sodium sulfate and concentrated in vacuo to leave 200 g of oil. This oil was heated overnight under reflux with 800 ml of concentrated hydrochloric acid. The reaction mixture was cooled and extracted three times with a one-third volume of ether. The ethereal extracts were combined, dried over magnesium sulfate, and concentrated in vacuo. The residue was crystallized from ether/hexane to give 86 g (49%) of crude product. This material was slurried with 500 ml of hexane to leave 76 g (44%) of 2,2-diethylsuccinic acid, mp 106°–109°.

EXAMPLE 16

Preparation of ethyl 2-cyano-3,3-diethylacrylate

A mixture of 473 g (5.5 mol) of 3-pentanone, 565 g (5 mol) of ethyl cyanoacetate, 60 g (1 mol) of acetic acid, 38.5 g (0.5 mol) of ammonium acetate and 500 ml of toluene was stirred and heated under a Dean-Stark trap for 7 hr. and then allowed to stand for 2 days at room temperature. The reaction mixture was washed three times with 1 l of water and concentrated on the rotary evaporator at a low temperature. The residue was distilled in vacuum to give 460 g of ethyl 2-cyano-3,3-diethylacrylate, bp 118°–120°/8 mm.

EXAMPLE 17

Preparation of acetylcyclopentane

To a solution of 35 g (0.35 mol) of chromium trioxide in 50 ml of water cooled in an ice bath was added 30.5 ml of concentrated sulfuric acid slowly with stirring. The precipitate was dissolved by the addition of 100 ml of water to give approximately 200 ml of solution which was cooled to 5° in an ice bath. Into a 500 ml r. b. flask fitted with mechanical stirrer, thermometer and dropping funnel was placed 25 g (0.22 mol) of 1-cyclopentylethanol and 120 ml of acetone. The reaction mixture was cooled to 5° and then treated with 90 ml of the chromic acid solution added at such a rate that the temperature did not exceed 20° which took approximately 10 min. The reaction mixture was stirred at 20°–25° for 1 hr and then treated with sodium bisulfite to neutralize the excess chromic acid. The top layer of the reaction mixture was separated. the bottom layer was extracted with 50 ml of pentane. This extracted was added to the original top layer. The bottom layer that formed was added to the original bottom layer, and this phase was extracted with 150 ml of pentane in three portions. The combined organic (top) layers were washed with 100 ml of brine in two portions, 100 ml of sodium bicarbonate in two portions and again with 100 ml of brine in two portions. This solution was dried over sodium sulfate and the pentane distilled off through a Vigreux column at atmospheric pressure. The residue was distilled at the water pump to give 16.1 g of acetylcyclopentane, bp 90°–93°/7.5 cm (nominal)

EXAMPLE 18

Preparation of Bromomethylcyclopropylketone

To a solution of 42 g (0.5 mol) of cyclopropylmethylketone in 625 ml of methanol cooled to 0°–5° in an ice bath was slowly added 29 ml (0.6 mol) of bromine. After the addition was complete, the cooling bath was removed, and the color disappeared accompanied by a gradual rise in temperature to 40°. The solution was diluted with 3 volumes of water, layered with ether and neutralized by the addition of saturated sodium bicarbonate solution. The aqueous phases was separated and extracted with ether in two portions. The organic phases were combined, washed with brine, dried over sodium sulfate and concentrated in vacuo to leave 80 g of crude bromomethylcyclopropylketone as an oil.

EXAMPLE 19

Preparation of Bromoacetylcyclopentane

To a solution of 16.1 g (0.143 mol) of acetylcyclopentane in 175 ml of methanol cooled in an ice bath was added 7.7 ml (0.15 mol) of bromine during 5 min. The reaction mixture was then allowed to warm to 10°–15° and held there by occasional application of the ice bath for 45 min until the reaction mixture became colorless. Then 100 ml of water was added and it was allowed to stir at room temperature for 0.5 hr. It was partially neutralized by the cautious addition of 10 g (72 mmol) of solid potassium carbonate, diluted with 200 ml of water and extracted with 4×150 ml of ether. The combined organic extracts were washed with 2×100 ml of saturated sodium bicarbonate solution and with 3×100 ml of water, dried over magnesium sulfate and concentrated in vacuo at room temperature to leave 30 g (110%) of bromoacetylcyclopentane as an oil whose nmr spectrum indicated that it was mainly the desired product.

EXAMPLE 20

Preparation of Bromoacetylcyclohexane

To a solution of 63.1 g (0.5 mol) of acetylcyclohexane in 625 ml of methanol cooled to 5° in an ice bath was added 29 ml (0.6 mol) of bromine during about 5 min. The cooling bath was removed and the temperature rose to 37°. The reaction mixture slowly formed a clear solution. This solution was poured in 1 l of water, made alkaline by the addition of saturated sodium bicarbonate solution and extracted with 500 ml of ether in two portions. The organic phases were combined, washed with 200 ml of water and with 200 ml of brine, dried over sodium sulfate and concentrated in vacuo to leave 108.4 of a pale oil whose nmr spectrum indicated it to contain somewhat more than 50% product.

EXAMPLE 21

Preparation of (E)-3-[2-[4-(cyclopentyl)-2-thiazolyl]ethenyl]benzeneamine

To a hot solution of 8.6 g (28.6 mmol) of (E)-4-cyclopentyl-2-[2-(3-nitrophenyl)ethenylthiazole in 50 ml of ethanol was added a hot solution of 21 g (93.1 mmol) of stannous chloride dihydrate in 50 ml of ethanol. An exothermic reaction ensued. The reaction was then heated on the steam bath for 45 min. After it had cooled slightly, to it was added 150 ml of 3 N sodium hydroxide, 50 ml of water and 100 ml of methylene chloride. A brown gum formed. The aqueous phase was separated and extracted with 200 ml of methylene chloride in two portions. The organic phases were combined, washed with 200 ml of water in two portions, dried over potassium carbonate and concentrated in vacuo. The residue was crystallized from hexane to give 7.3 g (94%) of (E)-3-[2-[4-(cyclopentyl)-2-thiazolyl]ethenyl]benzeneamine, mp 59°–61°.

Utilizing the above procedure the following compounds were prepared:
(a) from (E)-4-cyclobutyl-2-[2-(3-nitrophenyl)ethylthiazole, (E)-3-[2-[4-(cyclobutyl)-2-thiazolyl]ethenyl]-benzeneamine; and (b) from (E)-4-cyclohexyl-2-[2-(3-nitrophenyl)-ethenyl-thiazole, (E)-3-[2-[4-(cyclohexyl)-2-thiazolyl]ethenyl]-benzeneamine.

EXAMPLE 22

Preparation of
(E)-[N-[[3-[2-(4-Cyclobutyl-2-thiazolyl)-ethenyl]-phenyl]amino]-2-oxoethyl]-1-cyclopentane-1-carboxylic acid A mixture of 0.756 g of 1-carboxy-1-cyclopentaneacetic acid and 5 ml of acetyl chloride was heated to reflux for two hours. The mixture was then condensed by rotary evaporation followed by toluene flushes (2×) after which the residual materials were taken up in 25 ml of toluene. This solution was combined with a solution of 1.0 g of (E)-3-[2-[4-(cyclobutyl)-2-thiazolyl]ethenyl]benzenamine in 25 ml of toluene and the resulting solution was warmed on a steam bath for 30 min. Upon cooling a crystal crop was obtained which was isolated by filtration and ether wash to give 1.1 g of (E)-[N-[[3-[2-(4-cyclobutyl-2-thiazolyl)ethenyl]-phenyl]amino]-2-oxoethyl]-1-cyclopentane-1-carboxylic acid. Recrystallization from ethanol gave material of m.p. 188°–190° C.

EXAMPLE 23

Preparation of
(E)-3-[[[3-[2-(4-Cyclobutyl-2-thiazolyl)-ethenyl]phenyl]amino]carbonyl]-3-ethylpentanoic acid A mixture of 5.0 g of (E)-4-[[3-[2-(4-cyclobutyl-2-thiazolyl)ethenyl]phenyl]amino]-2,2-diethyl-4-oxobutanoic acid and 100 ml of acetyl chloride was heated to gentle reflux for 1.5 hr. The reaction mixture was then condensed by rotary evaporation and the residual materials were taken up in methylene chloride. This solution was washed with 5% sodium bicarbonate solution until neutral and then with sat. brine, dried (sodium sulfate) and condensed by rotary evaporation to yield 4.3 g of residual materials. 2.0 g of this material was solubilized along with 0.357 g of lithium hydroxide mono hydrate in 50 ml of 1:4 (V/V) water/methanol. This solution was heated to reflux for 1 hr. and then condensed to dryness by rotary evaporation. The residual materials were mixed with 50 ml of water, filtered, and the filtrate was acidified with dilute hydrochloric acid to yield 1.7 of (E)-3-[[[3-[2-(4-cyclobutyl-2-thiazolyl)ethenyl]phenyl]amino]carbonyl]-3-ethylpentanoic acid; m.p. 129°–13 ° C. after recrystallization from acetonitrile.

EXAMPLE 24

Preparation of
(E)-4-[[3-[2-(4-cyclobutyl-2-thiazolyl)-ethenyl]phenyl]amino]-4-oxobutanoic acid ethyl ester Ethyl succinyl chloride (0.56 ml) was added to an ice-bath cooled solution composed of 1.0 g of (E)-3-[2-[4-(cyclobutyl)-2-thiazolyl]ethenyl]benzenamine, 0.6 ml of triethylamine, and 10 ml of methylene chloride. After 1 hr, the reaction mixture was diluted with methylene chloride and washed with dilute hydrochloric acid, followed with water and sat. brine. The organic phase was separated and dried (Na2SO4). Condensation by rotary evaporation gave 1.5 g (E)-4-[[3-[2-(4-cyclobutyl-2-thiazolyl)ethenyl]phenyl]amino]-4-oxobutanoic acid ethyl ester; m.p. 98°–100° C. after recrystallization from ethyl acetate.

EXAMPLE 25

Preparation of
(E)-4-[[3-[2-(4-cyclobutyl-2-thiazolyl)-ethenyl]phenyl]amino]-2,2-diethyl-4-oxobutanoic acid trihydroxymethylaminomethane salt Tri-hydroxymethylaminomethane (121.4 mg) and 412.5 mg of (E)-4-[[3-[2-(4-cyclobutyl-2-thiazolyl)-ethenyl]phenyl]amino]-2,2-diethyl-4-oxobutanoic acid were dissolved in 10 ml of ethanol. This solution was then condensed by rotary evaporation to yield (E)-4-[[3-[2-(4-cyclobutyl-2-thiazolyl)ethenyl]phenyl]amino]-2,2-diethyl-4-oxobutanoic acid tri-hydroxymethylaminomethane salt as a free flowing solid after trituration with cold acetonitrile, m.p. 80°–87° C.

EXAMPLE 26

(E)-4-[[3-[2-(4-Cyclobutyl-2-thiazolyl)ethenyl]phenyl]amino]-2-cyclohexyl-4-oxobutanoic acid A mixture of 1.0 g of 2-cyclohexylsuccinic acid and 10 ml of acetyl chloride was warmed to reflux for two hours. The reaction mixture was then condensed by rotary evaporation with toluene chase (2×). The residual materials and 1.28 g of (E)-3-[2-[4-(cyclobutyl)-2-thiazolyl]ethenyl]benzeneamine were solubilized in 50 ml of toluene and the resulting solution was warmed on the steam bath for 0.5 hour. Upon cooling to room temperature a solid product formed. This material was isolated by filtration and recrystallized from acetonitrile to give 1.65 g of (E)-4-[[3-[2-(cyclobutyl-2-thiazolyl)ethenyl]phenyl]amino]-2-cyclohexyl-4-oxobutanoic acid; mp 205°–207° C.

EXAMPLE 27

(E)-4-[[3-[2-(Cyclobutyl-2-thiazolyl)ethenyl]phenyl]amino]-2-phenyl-4-oxobutanoic acid A mixture of 1.0 g of 2-phenylsuccinic acid and 10 ml of acetyl chloride was warmed to reflux for two hours. The reaction mixture was then condensed by rotary evaporation with toluene chase (2×). The residual materials and 1.4 g of (E)-3-[2-[4-(cyclobutyl)-2-thiazolyl]ethenyl]benzeneamine were solubilized in 50 ml of toluene and the resulting solution was warmed on the steam bath for 0.5 hour. Upon cooling to room temperature, the solids that formed were isolated by filtration. Recrystallization from acetonitrile gave 1.65 g of (E)-4-[[3-[2-(cyclobutyl-2-thiazolyl)-ethenyl]phenyl]amino]-2-phenyl-4-oxobutanoic acid; mp 202°–203° C.

EXAMPLE 28

Tablet Formulation (Wet Granulation)

| Item | Ingredient | mg/tablet | |
|---|---|---|---|
| | | 100 mg | 500 mg |
| 1. | (E)-4-[[3-[2-(4-cyclopropyl-2-thiazolyl)ethenyl]phenyl]-amino]-2,2-diethyl-4-oxobutanoic acid. | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| | Total | 167 | 836 |

Preparation of Tablets (1) Mix Items 1, 2, 3 and 4 and granulate with water.

(2) Dry the granulation at 50° C.

(3) Pass the granulation through suitable milling equipment.

(4) Add Item 5 and mix for three minutes; compress on a suitable press.

EXAMPLE 29

Capsule Formulation

| Item | Ingredient | mg/tablet | |
|---|---|---|---|
| | | 100 mg | 500 mg |
| 1. | (E)-4-[[3-[2-(4-cyclopropyl-2-thiazolyl)ethenyl]phenyl]-amino]-2,2-diethyl-4-oxobutan-oic acid. | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | Total | 117 | 582 |

Preparation of Capsules (1) Mix Items 1, 2 and 3 and wet granulate with water. Dry at 45° C. overnight.

(2) Mill through suitable screen using appropriate milling equipment.

(3) Add Items 4 and 5 and mix for five minutes.

EXAMPLE 30

Capsule Formulation

| Ingredients | mg/capsule | | | |
|---|---|---|---|---|
| 1. (E)-4-[[3-[2-(4-cyclopropyl-2-thiazolyl)-ethenyl]phenyl]-amino]-2,2-diethyl-4-oxobutanoic acid. | 0.01 | 0.5 | 5.0 | 25.0 |
| 2 Lactose Hydrous | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 1.0 |
| Total | 200.0 | 200.0 | 200.0 | 200.0 |

Preparation of Capsules (1) Mix Items 1, 2 and 3 in a suitable mixer for 30 minutes.

(2) Add Items 4 and 5 and mix for 3 minutes.

(3) Fill into suitable capsule.

EXAMPLE 31

Wet Granulation Formulation

| Ingredients | mg/capsule | | | |
|---|---|---|---|---|
| 1. (E)-4-[[3-[2-(4-cyclopropyl-2-thiazolyl)-ethenyl]phenyl]-amino]-2,2-diethyl-4-oxobutanoic acid. | 0.01 | 0.5 | 5.0 | 25.0 |
| 2. Lactose Anhydrous DTG | 106.99 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Stearate | 1.0 | 1.0 | 1.0 | 2.0 |
| Total | 130.0 | 130.0 | 130.0 | 130.0 |

Preparation of Capsules (1) Dissolve Item 1 in a suitable solvent such as alcohol.

(2) Spread the solution in Step 1 over Item 2, dry.

(3) Add Items 3 and 4 and mix for 10 minutes.

(4) Add magnesium stearate and mix for 3 minutes and compress.

EXAMPLE 32

Cream 0.5%

| Ingredients | g/kg | Reasonable Variations |
|---|---|---|
| (E)-4-[[3-[2-(4-cyclopropyl-2-thiazolyl)ethenyl]phenyl]-amino]-2,2-diethyl-4-oxobutanoic acid. | 5.150* | — |
| Glyceryl Monostearate S.E.[1] | 100.00 | 80–120 |
| Polysorbate 60[2] | 20.00 | 15–25 |
| Cetyl Alcohol | 50.00 | 40–60 |
| Petrolatum | 70.00 | 50–90 |
| Methylparaben | 1.50 | 1.25–1.75 |
| Propylparaben | 0.50 | 0.4–0.06 |
| Propylene Glycol | 200.00 | 150–250 |
| Purified Water | 568.05 | 475–575 |
| TOTAL | 1,015.20 | |

*3% excess
[1] Arlacel 165
[2] Tween 60

Preparation of Cream (1) Dissolve (E)-4-[[3-[2-(4-cyclopropyl-2-thiazolyl)-ethenyl]phenyl]amino]-2,2-diethyl-4-oxobutanoic acid in propylene glycol, add methyl paraben, propyl paraben and water and heat to 70° C.

(2) Melt petrolatum, glyceryl monstearate S.E., and cetyl alcohol. Heat to 70° C. Add polysorbate 80 and mix.

(3) Add solution in Step 2 to solution in Step 1 at 70° C. cool to room temperature while stirring.

EXAMPLE 33

Inhalation Aerosol Formulation (Solution)

| Item | Ingredients | % w/w |
|---|---|---|
| 1. | (E)-4-[[3-[2-(4-cyclopropyl-2-thiazolyl)ethenyl]phenyl]-amino]-2,2-diethyl-4-oxobutanoic acid. | 1.0 |
| 2. | Ethyl Alcohol | 30.0 |
| 3. | Ascorbic Acid | 0.5 |
| 4. | Freon 12 | 54.8 |
| 5. | Freon 114 | 13.7 |
| | Total | 100% |

Preparation of Aerosol (1) Dissolve Items 1 and 3 in Item 2.

(2) Fill solution from Step 1 into a suitable glass bottle, insert valve and crimp to seal container.

(3) Pressure-fill a 80:20 mixture of Items 4 and 5 into the container.

NOTE: A suitable valve may be used to deliver 25 to 100 microliters in volume.

EXAMPLE 34

Inhalation Aerosol Formulation (Suspension)

| Item | Ingredients | % w/w |
|---|---|---|
| 1. | (E)-4-[[3-[2-(4-cyclopropyl-2-thiazolyl)ethenyl]phenyl]-amino]-2,2-diethyl-4-oxobutanoic acid. (micronized) | 1.0 |
| 2. | Sorbitan Trioleate | 0.5 |
| 3. | Freon 12 | 64.0 |
| 4. | Freon 11 | 18.5 |
| 5. | Freon 114 | 16.0 |
|  | Total | 100% |

Preparation of Aerosol (1) Mix Items 1 and 2 into 4 and homogenize.

(2) Fill the concentrate suspension from Step 1 into a suitable can and place in valve and crimp to seal container.

(3) Pressure-fill a 80:20 mixture of Items 3 and 5.

NOTE: A suitable valve may be used to deliver 25 to 100 microliters in volume.

What is claimed is:

1. A compound of the formula

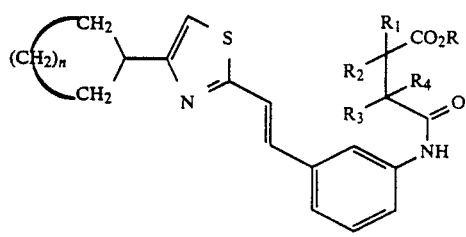

wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy or halogen, or $R_1$ and $R_2$ taken together with the carbon atom are alkylene of 2 to 5 carbon atoms unsubstituted or substituted by lower alkyl, and n is an integer of from 0 to 3, and, when $R_1$ is different from $R_2$ and/or $R_3$ is different from $R_4$, an enantiomer, a diastereomer or a racemate thereof, or, when R is hydrogen, a salt thereof with a pharmaceutically acceptable base.

2. A compound in accordance with claim 1, wherein R is hydrogen, $R_1$ and $R_2$, independently, are lower alkyl, $R_3$ and $R_4$ are hydrogen and n is 0 to 3.

3. A compound in accordance with claim 1, wherein R is hydrogen, $R_1$ and $R_2$, independently, are lower alkyl, $R_3$ and $R_4$ are hydrogen and n is 1.

4. A compound in accordance with claim 1, (E)-4-[[3-[2-(4-cyclobutyl-2-thiazolyl)ethenyl]phenyl]amino]-2,2-diethyl-4-oxobutanoic acid.

5. A compound in accordance with claim 1, (E)-4-[[3-[2-(4-cyclopropyl-2-thiazolyl)ethenyl]phenyl]amino]-2,2-diethyl-4-oxobutanoic acid.

6. A compound in accordance with claim 1, (E)-4-[[3-[2-(4-cyclopentyl-2-thiazolyl)ethenyl]phenyl]amino]-2,2-diethyl-4-oxobutanoic acid.

7. A pharmaceutical composition comprising an amount of a compound of the formula

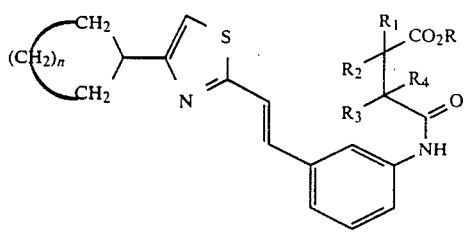

effective for treating bronchopulmonary constriction wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy or halogen, or $R_1$ and $R_2$ taken together with the carbon atom are alkylene of 2 to 5 carbon atoms unsubstituted or substituted by lower alkyl, and n is an integer of from 0 to 3 and, when $R_1$ is different from $R_2$ and/or $R_3$ is different from $R_4$, an enantiomer, a diastereomer or a racemate thereof, or, when R is hydrogen, a salt thereof with a pharmaceutically acceptable base, and an inert carrier material.

8. A pharmaceutical composition in accordance with claim 7, wherein R is hydrogen, $R_1$ and $R_2$, independently, are lower alkyl, $R_3$ and $R_4$ are hydrogen and n is 0 to 3.

9. A pharmaceutical composition in accordance with claim 7, wherein R is hydrogen, $R_1$ and $R_2$, independently, are lower alkyl, $R_3$ and $R_4$ are hydrogen and n is 1.

10. A pharmaceutical composition in accordance with claim 7, wherein the compound of formula I is (E)-4-[[3-[2-(4-cyclobutyl-2-thiazolyl)ethenyl]phenyl]-amino]-2,2-diethyl-4-oxobutanoic acid.

11. A pharmaceutical composition in accordance with claim 7, wherein the compound of formula I is (E)-4-[[3-]2-(4-cyclopropyl-2-thiazolyl)ethenyl]phenyl-]amino]-2,2-diethyl-4-oxobutanoic acid.

12. A pharmaceutical composition in accordance with claim 7, wherein the compound of formula I is (E)-4-[[3-]2-(4-cyclopentyl-2-thiazolyl)ethenyl]phenyl-]amino-2,2-diethyl-4-oxobutanoic acid.

13. A method of treating bronchopulmonary constriction which comprises administering to a host requiring such treatment an effective amount of a compound of formula I

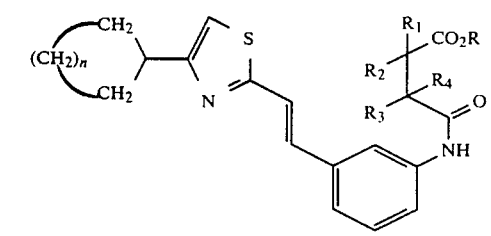

wherein R is hydrogen or lower alkyl, $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy or halogen, or $R_1$ and $R_2$ taken together with the carbon atom are alkylene of 2 to 5 carbon atoms unsubstituted or substituted by lower alkyl, and n is an integer of from 0 to 3, and, when $R_1$ is different from $R_2$ and/or $R_3$ is different from $R_4$, an enantiomer, a diastereomer or a racemate thereof, or, when R is hydrogen, a salt thereof with a pharmaceutically acceptable base.

14. A method in accordance with claim 13, wherein R is hydrogen, $R_1$ and $R_2$, independently, are lower alkyl, $R_3$ and $R_4$ are hydrogen and n is 0 to 3.

15. A method in accordance with claim 13, wherein R is hydrogen, $R_1$ and $R_2$, independently, are lower alkyl, $R_3$ and $R_4$ are hydrogen and n is 1.

16. A method in accordance with claim 13, wherein the compound of formula I is (E)-4-[[3-[2-(4-cyclobutyl-2-thiazolyl)ethenyl]phenyl]amino]]-2,2-diethyl-4-oxobutanoic acid.

17. A method in accordance with claim 13, wherein the compound of formula I is (E)-4-[[3-[2-(4-cyclopropyl-2-thiazolyl)ethenyl]phenyl]amino]-2,2-diethyl-4-oxobutanoic acid.

18. A method in accordance with claim 13, wherein the compound of formula I is (E)-4-[[3-[2-(4-cyclopentyl-2-thiazolyl)ethenyl]phenyl]amino]-2,2-diethyl-4-oxobutanoic acid.

* * * * *

UNITED STATES PATENT AND TRADEMARK OFFICE
CERTIFICATE OF CORRECTION

PATENT NO. : 5,001,140
DATED : 3/19/91
INVENTOR(S) : Field et al.

It is certified that error appears in the above-identified patent and that said Letters Patent is hereby corrected as shown below:

Claim 12, Column 24, line 46
"[[3-] 2" should be --- [[3- [2- ---.

Claim 12, Column 24, lines 46 & 47
"phenyl -] amino" should be --- phenyl] amino---

Signed and Sealed this

Eighth Day of September, 1992

Attest:

DOUGLAS B. COMER

*Attesting Officer*   *Acting Commissioner of Patents and Trademarks*